United States Patent [19]
Bourzat et al.

[11] Patent Number: 5,374,656

[45] Date of Patent: * Dec. 20, 1994

[54] N-PHENYL-N-ALKOXYCARBONYLALKYL GLYCINAMIDES, THEIR PREPARATION AND THE MEDICAMENTS CONTAINING THEM

[75] Inventors: Jean-Dominique Bourzat, Vincennes; Marc Capet, Thiais; Claude Cotrel, Paris; Claude Guyon, Saint Maur des Fosses; Franco Manfre, Vitry sur Seine; Gérard Roussel, Soisy sur Seine, all of France

[73] Assignee: Rhone-Poulenc Rorer, S.A., France

[*] Notice: The portion of the term of this patent subsequent to Jun. 29, 2010 has been disclaimed.

[21] Appl. No.: 862,760

[22] PCT Filed: Feb. 14, 1991

[86] PCT No.: PCT/FR91/00119

§ 371 Date: Jun. 25, 1992

§ 102(e) Date: Jun. 25, 1992

[87] PCT Pub. No.: WO91/12265

PCT Pub. Date: Aug. 22, 1991

[30] Foreign Application Priority Data

Feb. 19, 1990 [FR] France .................. 90 01961

[51] Int. Cl.$^5$ ............ A61K 31/325; C07C 205/00; C07C 229/00
[52] U.S. Cl. ................. 514/542; 560/9; 560/21; 560/34; 560/39; 560/41
[58] Field of Search ............ 560/41, 9, 21, 34, 39, 560/41; 514/542

[56] References Cited

FOREIGN PATENT DOCUMENTS 89-6250 2/1990 France .

OTHER PUBLICATIONS

Chemical Abstracts Service, CA114(17):164819x (1994).
Peptides, Structure and Function, Proceedings of the Ninth American Peptide Symposium, 1985, Pierce Chemical Company.
Chem. Abs., vol. 105, 1986, p. 801, abstract 173038h.
Chem. Abs., vol. 113, 1990, T. Lu, et al., "Synthesis of disulfides of N-(N-(2-mercaptobenzoyl)glycl)-N-alkyl/aryl-glycine", p. 784, abstract 231990r.

Primary Examiner—Johann Richter
Assistant Examiner—Catherine Scalzo
Attorney, Agent, or Firm—Morgan & Finnegan

[57] ABSTRACT

This invention relates to compounds of formula:

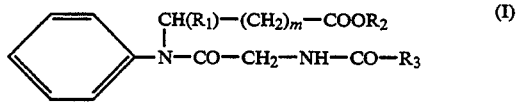

in which
$R_1$ represents a hydrogen atom or an alkyl or alkoxycarbonyl radical or an unsubstituted or substituted phenyl radical,
$R_2$ represents an alkyl (1–8 C) or polyfluoroalkyl radical or an unsubstituted or substituted cycloalkyl radical,
$R_3$ represents an unsubstituted or substituted phenyl radical, a naphthyl, indolyl, quinolyl or phenylamino radical in which the phenyl ring is optionally substituted, or a quinolylamino radical, and
m is 0 or 1, the process for preparing them and the medicaments containing them.

6 Claims, No Drawings

N-PHENYL-N-ALKOXYCARBONYLALKYL GLYCINAMIDES, THEIR PREPARATION AND THE MEDICAMENTS CONTAINING THEM

DESCRIPTION OF THE INVENTION

The present invention relates to compounds of formula:

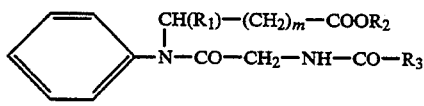

their preparation and the medicaments containing them.

In formula (I), $R_1$ represents a hydrogen atom or an alkyl or alkoxycarbonyl radical or a phenyl radical which is unsubstituted or substituted by one or more substituents chosen from halogen atoms and alkyl, alkoxy, nitro, amino and alkylthio radicals, $R_2$ represents an alkyl (1-8 C), polyfluoroalkyl or cinnamyl radical or a cycloalkyl radical which is unsubstituted or substituted by one or more alkyl radicals, $R_3$ represents a phenyl radical (unsubstituted or substituted by one or more substituents chosen from alkyl, alkoxy and alkylthio radicals and halogen atoms), a naphthyl, indolyl, quinolyl or phenylamino radical (in which the phenyl ring is optionally substituted by one or more substituents chosen from halogen atoms and alkyl, alkoxy and alkylthio radicals) or a quinolylamino radical, and m is 0 or 1, it being understood that when $R_1$ represents a hydrogen atom or an alkyl or phenyl radical, $R_3$ represents a naphthyl, indolyl or phenylamino radical, optionally substituted by an alkyl, alkoxy or alkylthio radical or by one or two halogen atoms, and m is 0, $R_2$ is not an alkyl radical containing 1 to 4 carbon atoms or a cycloalkyl radical.

In the definitions above and in those which will be given below, unless indicated to the contrary, the alkyl and alkoxy radicals and the alkyl and alkoxy portions contain 1 to 4 carbon atoms in a straight or branched chain and the cycloalkyl radicals contain 3 to 6 carbon atoms.

In formula (I), the halogen atoms are preferably chlorine, bromine or fluorine atoms.

The compounds of formula (I) containing one or more centers of asymmetry have isomeric forms. The racemates and the enantiomers of these compounds also form part of the invention.

The compounds of formula (I) for which $R_3$ represents a phenylamino radical in which the phenyl ring is optionally substituted may be prepared by the action of an acid of formula:

$$HOOC-CH_2-NH-CO-R_3 \qquad (II)$$

in which $R_3$ has the same meanings as above, on an amine of formula:

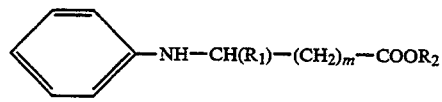

in which m, $R_1$ and $R_2$ have the same meanings as in formula (I).

This reaction generally takes place in an inert solvent, such as a chlorinated solvent (chloroform, dichloromethane or 1,2-dichloroethane for example), by means of thionyl chloride, at the boiling point of the solvent.

The acids of formula (II) may be obtained by the action of a phenyl isocyanate in which the phenyl ring is optionally substituted by one or more substituents chosen from halogen atoms and alkyl, alkoxy and alkylthio radicals, on a derivative of formula:

$$HOOC-CH_2-NH_2 \qquad (IV)$$

This reaction generally takes place in an aqueous medium, in the presence of an alkaline agent, such as an alkali metal bicarbonate, at a temperature of between 15 and 30° C.

The amines of formula (III) for which m is 0 may be obtained by the action of aniline on a derivative of formula:

$$Hal-CH(R_1)-(CH_2)_m-COOR_2 \qquad (V)$$

in which $R_1$ has the same meanings as in formula (I), m is 0 and Hal represents a halogen atom (preferably chlorine or bromine).

This reaction preferably takes place in an inert solvent, such as acetonitrile, dimethylformamide or tetrahydrofuran, at the boiling point of the solvent.

The derivatives of formula (V) for which $R_1$ represents an alkyl, alkoxycarbonyl or substituted phenyl radical may be obtained by halogenation of a derivative of formula:

$$HCH(R_1)-(CH_2)_m-COOR_2 \qquad (VI)$$

in which $R_1$ has the same meanings as above, $R_2$ has the same meanings as in formula (I) and m is 0.

This halogenation takes place by means of a halogenating agent such as N-bromosuccinimide, N-chlorosuccinimide or bromine, if appropriate in the presence of azobisisobutyronitrile, or acetamide, in an inert solvent, such as a chlorinated solvent (chloroform or carbon tetrachloride for example), at a temperature between 20° C. and the boiling point of the solvent.

The derivatives of formula (VI) may be obtained by the action of an alcohol of formula:

$$HOR_2 \qquad (VII)$$

in which $R_2$ has the same meanings as in formula (I), on an acid of formula:

$$HCH(R_1)-(CH_2)_m-COOH \qquad (VIII)$$

in which $R_1$ has the same meanings as in formula (VI) and m is 0, or a reactive derivative of this acid, such as a halide.

When the acid is used, the reaction is carried out in the presence of an acid such as sulphuric acid, at the boiling point of the reaction medium.

When a halide is used, the reaction is carried out in the presence of a tertiary amine, such as triethylamine or N,N-dimethylaniline, at a temperature close to 20° C.

The derivatives of formula (VIII) for which $R_1$ represents an alkoxycarbonyl radical may be obtained by application or adaptation of the method described in Acta Chem. Scand., B29, 687 (1975).

The derivatives of formula (V) for which m is 0 may also be obtained by the action of an alcohol of formula (VII) on a dihalogenated derivative of formula:

Hal—CH($R_1$)—($CH_2$)$_m$—COHal          (IX)

in which $R_1$ has the same meanings as in formula (I), m is 0 and Hal represents a halogen atom.

This reaction takes place in the presence of a tertiary amine such as triethylamine or N,N-dimethylaniline, at a temperature of between 0 and 30° C., in an inert solvent, such as a chlorinated solvent (chloroform or 1,2-dichloroethane for example) or an ether (diethyl ether for example).

The dihalogenated derivatives of formula (IX) may be obtained by halogenation of a derivative of formula:

HCH($R_1$)—($CH_2$)$_m$—COHal          (X)

in which $R_1$ has the same meanings as in formula (I), m is 0 and Hal represents a halogen atom.

This halogenation generally takes place under the conditions mentioned above for the halogenation of compounds of formula (VI).

The derivatives of formula (X) may be obtained by halogenation of the corresponding acids by any method known to those skilled in the art for converting an acid to an acid halide. Preferably, the reaction is carried out using thionyl chloride or thionyl bromide.

The derivatives of formula (X) for which $R_1$ represents an alkoxycarbonyl radical may also be obtained by application or adaptation of the method described in Beilstein, 2,582.

The amines of formula (III) for which m is 1 may be obtained by reduction of a derivative of formula:

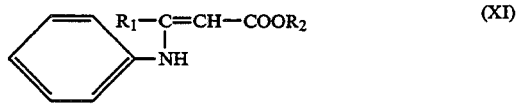

(XI)

in which $R_1$ and $R_2$ have the same meanings as in formula (I).

This reaction generally takes place in an inert solvent such as tetrahydrofuran, using trifluoroacetic acid and sodium cyanoborohydride in solution in methanol, at a temperature close to 0° C.

The derivatives of formula (XI) may be obtained by application or adaptation of the method described by F. Texier-Boullet, Synthesis, 679 (1985).

The compounds of formula (I) for which $R_3$ represents a phenylamino radical in which the phenyl ring is optionally substituted, or a quinolylamino radical, may also be prepared by the action of an amino derivative of formula:

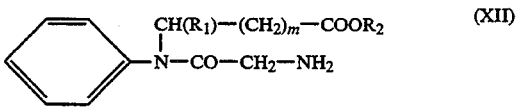

(XII)

in which $R_1$, $R_2$ and m have the same meanings as in formula (I), on one a derivative of formula:

$R_4$—NH—COOCCl$_3$          (XIII)

in which $R_4$ represents a phenyl radical (optionally substituted by one or more substituents chosen from halogen atoms and alkyl, alkoxy and alkylthio radicals) or a quinolyl radical.

This reaction generally takes place in an inert solvent, such as a chlorinated solvent (chloroform or dichloromethane for example) or an aromatic solvent (benzene or toluene for example), at a temperature close to 20° C.

The amino derivatives of formula (XII) may be obtained by the action of hydrazine or methylhydrazine on a derivative of formula:

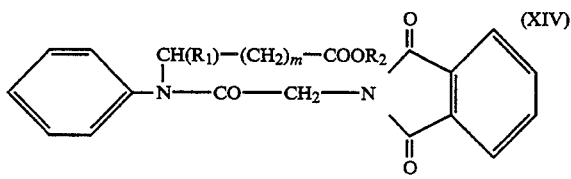

(XIV)

in which $R_1$, $R_2$, and m have the same meanings as in formula (I).

This reaction generally takes place in an inert solvent such as an alcohol (methanol or ethanol for example) or a chlorinated solvent (dichloromethane or chloroform for example), at a temperature between 0° C. and the boiling point of the solvent.

The derivatives of formula (XIV) may be obtained by the action of a chloride of formula:

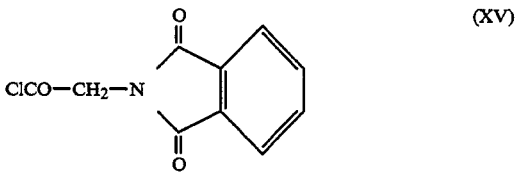

(XV)

on a derivative of formula (III) in which $R_1$, $R_2$ and m have the same meanings as in formula (I).

This reaction generally takes place in an inert solvent such as a chlorinated solvent (chloroform or 1,2-dichloroethane for example), in the presence of an alkaline agent such as an alkali metal bicarbonate, at a temperature between 20° C. and the boiling point of the solvent.

The chloride of formula (XV) may be obtained by application of the method described by W. Grassmann et al., Chem. Ber., 83, 244 (1950).

The derivatives of formula (XIII) may be obtained by the action of trichloromethyl chloroformate on an amine of formula:

$R_4$—NH$_2$          (XVI)

in which $R_4$ has the same meanings as in formula (XIII).

This reaction preferably takes place in an inert solvent, such as a chlorinated solvent (chloroform or dichloromethane for example), in the presence of a base such as a trialkylamine, at a temperature close to 0° C.

The compounds of formula (I) for which $R_3$ represents an optionally substituted phenyl radical or a naphthyl, indolyl or quinolyl radical may be prepared by the action of an amino derivative of formula (XII) on an acid of formula:

$$HOOC-R_3 \quad (XVII)$$

in which $R_3$ has the same meanings as above, or a reactive derivative of this acid.

When the acid is used, the reaction is carried out in the presence of a peptide condensing agent, such as a carbodiimide (for example dicyclohexylcarbodiimide or N,N'-carbonyldiimidazole), in an inert solvent, such as an ether (for example tetrahydrofuran or dioxane), an amide (dimethylformamide for example) or a chlorinated solvent (chloroform or dichloromethane for example) at a temperature between 0° C. and the boiling point of the solvent.

When a derivative of the acid is used, it is possible to carry out the reaction with the anhydride, a mixed anhydride, an acid halide or an ester (which may be chosen from the activated or nonactivated esters of the acid). The reaction is then carried out either in an organic medium, if appropriate in the presence of an acid acceptor such as a nitrogenous organic base (for example a trialkylamine, a pyridine, 1,8-diazabicyclo[5.4.-0]undec-7-ene or 1,5-diazabicyclo[4.3.0]non-5-ene), in a solvent as mentioned above or in a mixture of these solvents, at a temperature between 0° C. and the reflux temperature of the reaction mixture; or in a two-phase aqueous-organic medium in the presence of an alkali metal or alkaline earth metal base (sodium hydroxide or potassium hydroxide) or an alkali metal or alkaline earth metal carbonate or bicarbonate, at a temperature of between 0 and 40° C.

The compounds of formula (I) may also be prepared by esterification of an acid of formula:

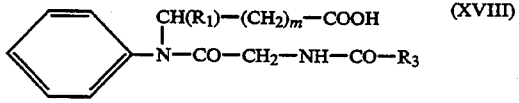

in which $R_1$, $R_3$ and m have the same meanings as in formula (I), by means of an alcohol of formula (VII).

This esterification generally takes place in an inert solvent, such as a chlorinated solvent (chloroform or methylene chloride for example), in the presence of a base such as a trialkylamine and 1-benzotriazinyloxy-tris(dimethylamino)phosphonium hexafluorophosphonate, at a temperature close to 25° C.

The corresponding acid may be obtained by hydrolysis of a compound of formula (I).

This hydrolysis generally takes place in a chlorinated solvent, such as chloroform or methylene chloride, by means of trifluoroacetic acid, at the boiling point of the solvent.

The compounds of formula (I) for which $R_1$ represents a phenyl radical substituted by an amino radical may also be prepared by reduction of the corresponding nitro derivative.

This reduction may be carried out, in particular, by means of iron in powder form and hydrochloric acid in an alcohol/water mixture, at the boiling point of the reaction medium.

Those skilled in the art will understand that, in order to carry out the processes according to the invention described above, it may be necessary to introduce groups which protect the amino groups in order to prevent secondary reactions. These amino groups may, for example, be blocked in the form of trifluoromethylacetamide and then regenerated by the action of ammoniacal methanol after having carried out the process according to the invention.

The enantiomers of the compounds of formula (I) containing at least one site of asymmetry may be obtained by resolution of the racemates, for example by chiral column chromatography using the method of W. H. Pirckle et al., asymetric synthesis, vol. 1, Academic Press (1983) or by synthesis from chiral precursors.

The compounds of formula (I) may be purified by the customary known methods, for example by crystallization, chromatography or extraction.

The compounds of formula (I) have valuable pharmacological properties. These compounds possess a strong affinity for cholecystokinin (CCK) receptors and gastrin and are therefore useful in the treatment and the prevention of disorders associated with CCK and gastrin in the nervous system and the gastrointestinal system.

Thus, these compounds may be used for the treatment or the prevention of psychoses, anxiety disorders, Parkinson's disease, tardive dyskinesia, irritable colon syndrome, acute pancreatitis, ulcers and disorders of the intestinal motility and some tumors of the lower oesophagus, the colon and the intestine and as an appetite regulator. These compounds also have a boosting effect on the analgesic activity of narcotic and nonnarcotic medicaments.

The affinity of the compounds of formula (I) for the CCK receptors was determined by a technique inspired by that of A. Saito et al. (J. Neuro. Chem. 37, 483–490 (1981)) in the cerebral cortex and the pancreas.

In these tests, the $IC_{50}$ of the compounds of formula (I) is generally less than or equal to 1000 nM.

It is known, furthermore, that the products which recognize the central receptors of CCK have a similar specificity for the gastrin receptors in the gastrointestinal tract (Bock et al., J. Medo Chem., 32, 16–23 (1989); Reyfeld et al., Am. J. Physiol., 240, G255–266 (1981); Beinfeld et al., Neuropeptides, 3, 411–427 (1983)).

The compounds of formula (I) have a low toxicity. Their $LD_{50}$ is generally higher than 40 mg/kg administered subcutaneously to mice.

The compounds of formula (I) for which:

$R_1$ represents a hydrogen atom or an alkoxycarbonyl radical or a phenyl radical optionally substituted by one or more substituents chosen from halogen atoms and alkoxy, nitro and amino radicals, $R_2$ represents an alkyl, polyfluoroalkyl or cinnamyl radical or a cycloalkyl radical which is unsubstituted or substituted by one or more alkyl radicals, $R_3$ represents a phenyl radical substituted by an alkyl radical or by a halogen atom, or a quinolyl radical, and m is 0 or 1 are of particular value.

The following compounds are particularly valuable:
tert-butyl (RS)-2-(4-aminophenyl)-4-{2-[3-(3-methylphenyl)ureido]-N-phenylacetamido}acetate
tert-butyl (RS)-2-(3-chlorophenyl)-2-{2-[3 -(3-methylphenyl)ureido]-N-phenylacetamido}acetate
tert-butyl (RS)-2-(2-chlorophenyl)-2-{2-[3-(3-methylphenyl)ureido]-N-phenylacetamido}acetate
tert-butyl (RS)-2-(3-fluorophenyl)-2-{2-[3-(3-methylphenyl)ureido]-N-phenylacetamido}acetate.

EXAMPLES

The following examples illustrate the invention without restricting it.

Example 1

A suspension of 3.77 g of 1,1,1,3,3,3-hexafluoro-2-propyl (RS)-2-anilino-2-phenylacetate and 2.08 g of 2-[3-(3-methylphenyl)ureido]acetic acid in 50 cm³ of anhydrous 1,2-dichloroethane is heated to reflux. 1.18 g of thionyl chloride is then added, maintaining reflux until the evolution of gas has ceased. The reaction mixture is then poured into 30 cm³ of a saturated aqueous sodium bicarbonate solution and 50 cm³ of methylene chloride are then added. The organic phase is washed with 50 cm³ of water, dried over magnesium sulphate and concentrated to dryness under reduced pressure (2.7 kPa) at 40° C. The product is purified by chromatography on 100 g of silica (0,063–0,200 mm) contained in a column 3.5 cm in diameter [eluent: methylene chloride/methanol (99/1 by volume)] collecting 50-cm³ fractions. Fractions 14 to 22 are combined and concentrated to dryness under reduced pressure (2.7 kPa) at 40° C. After recrystallization from acetonitrile, 2.5 g of 1,1,1,3,3,3-hexafluoro-2-propyl (RS)-2-{2-[3-(3-methylphenyl)ureido]-N-phenylacetamido}phenylacetate melting at 160° C. are obtained.

1,1,1,3,3,3-Hexafluoro-2-propyl (RS)-2-anilino-2-phenylacetate may be prepared in the following way: 16.1 g of 1,1,1,3,3,3-hexafluoro-2-propyl (RS)-α-bromophenylacetate are added to a solution of 10.24 g of aniline in 150 cm³ of acetonitrile and the mixture is stirred under reflux for 3 hours. The insoluble product is separated off by filtration and the filtrate is concentrated to dryness under reduced pressure (2.7 kPa) at 40° C. The product obtained is purified by chromatography on 100 g of silica (0.063–0.200 mm) contained in a column 2.7 cm in diameter [eluent: cyclohexane/ethyl acetate 90/10 by volume)], collecting 40-cm³ fractions. Fractions 5 to 18 are combined and concentrated to dryness under reduced pressure (2.7 kPa) at 40° C. 12 g of 1,1,1,3,3,3-hexafluoro-2-propyl (RS)-2-anilino-2-phenylacetate are then obtained in the form of an oil which is used as such in the subsequent syntheses.

1,1,1,3,3,3-Hexafluoro-2-propyl (RS)-α-bromophenylacetate may be prepared in the following way: 14 g of α-bromophenylacetyl chloride are added in the course of 20 minutes to a solution of 10 g of 1,1,1,3,3,3-hexafluoro-2-propanol and 6.6 g of triethylamine in 80 cm³ of diethyl ether, kept at a temperature close to 5° C., and the mixture is then stirred for 2 hours at a temperature close to 25° C. The insoluble product is separated off by filtration and the filtrate is washed successively with 20 cm³ of a 4N aqueous hydrochloric acid solution, 20 cm³ of a saturated aqueous sodium bicarbonate solution and 25 cm³ of water and then dried over magnesium sulphate and concentrated to dryness under reduced pressure (2.7 kPa) at 30° C. 16.1 g of 1,1,1,3,3,3-hexafluoro-2-propyl (RS)-α-bomophenylacetate are then obtained in the form of an oil which is used as such in the subsequent syntheses.

2-[3-(3-Methylphenyl)ureido]acetic acid may be prepared in the following way: 53 g of 3-methylphenyl isocyanate are added in the course of 15 minutes to a solution of 30 g of glycine and 53 g of sodium bicarbonate in 600 cm³ of water. The reaction mixture is stirred for 4 hours at a temperature close to 25° C. and then washed with 200 cm³ of ethyl acetate and acidified to pH 1 with 200 cm³ of a 4N hydrochloric acid solution. The product is separated off by filtration, washed with water and dried in air. 72 g of 2-[3-(3-methylphenyl)ureido]acetic acid melting at 208° C. are then obtained.

Example 2

Following a procedure analogous to that described in Example 1, but using 4.8 g of 1-methylcyclopentyl 2-anilinoacetate, 4.1 g of 2-[3-(3-methylphenyl)ureido]acetic acid and 1.4 cm³ of thionyl chloride as starting materials, 0.6 g of 1-methylcyclopentyl 2-{2-[3-(3-methylphenyl)ureido]-N-phenylacetamido}acetate melting at 160° C. is obtained after recrystallization from an acetonitrile/diisopropyl ether mixture (40/60 by volume).

1-Methylcyclopentyl 2-anilinoacetate may be prepared in a manner analogous to that described in Example 1 for the preparation of 1,1,1,3,3,3-hexafluoro-2-propyl (RS)-2-anilino-2-phenylacetate, but using 5.7 g of 1-methylcyclopentyl bromoacetate and 4.6 g of aniline as starting materials. The product is purified by chromatography on 70 g of silica (0.063–0.200 mm) contained in a column 2 cm in diameter [eluent: cyclohexane/ethyl acetate (70/30 by volume)] collecting 20-cm³ fractions. Fractions 3 to 6 are combined and concentrated to dryness under reduced pressure (2.7 kPa) at 40° C. 4.8 g of 1-methylcyclopentyl 2-anilinoacetate are then obtained in the form of an oil which is used as such in the subsequent syntheses.

1-Methylcyclopentyl bromoacetate may be prepared in the following way: 8.4 g of bromoacetyl bromide are added in the course of 5 minutes to a solution of 10 g of 1-methylcyclopentanol and 12 g of N,N-dimethylaniline in 100 cm³ of 1,2-dichloroethane, kept at a temperature close to 0° C. The reaction mixture is stirred at a temperature close to 25° C. for 16 hours and washed successively with twice 25 cm³ of a 4N aqueous hydrochloric acid solution, 25 cm³ of water and 25 cm³ of a saturated aqueous sodium bicarbonate solution. The organic phase is dried over magnesium sulphate and concentrated to dryness under reduced pressure (2.7 kPa) at 40° C. The product obtained is purified by chromatography on 120 g of silica (0.063–0.200 mm) contained in a column 3.0 cm in diameter (eluent: dichloromethane), collecting 20-cm³ fractions. Fractions 2 to 4 are combined and concentrated to dryness under reduced pressure (2.7 kPa) at 40° C. 5.7 g of 1-methylcyclopentyl bromoacetate are then obtained in the form of an oil which is used as such in the subsequent syntheses.

Example 3

The procedure is carried out in a manner analogous to that described in Example 1, but using 4.8 g of 2-methylcyclohexyl (1RS,2SR)-2-anilinoacetate, 4.0 g of 2-[3-(3-methylphenyl)ureido]acetic acid and 1.4 cm³ of thionyl chloride as starting materials. After recrystallization from an acetonitrile/diisopropyl ether mixture (40/60 by volume), 2.0 g of 2-methylcyclohexyl (1RS,2SR)-2-{2-[3-(3-methylphenyl)ureido]-N-phenylacetamido}acetate melting at 140° C. are obtained.

2-Methylcyclohexyl (1RS,2SR)-2-anilinoacetate may be prepared in a manner analogous to that described in Example 1 for the preparation of 1,1,1,3,3,3-hexafluoro-2-propyl (RS)-2-anilino-2-phenylacetate, but using 4.7 g of (1RS,2SR)-2-methylcyclohexyl bromoacetate and 3.7 g of aniline as starting materials. The product obtained is purified by chromatography on 40 g of silica (0.063–0.200 mm) contained in a column 1.5 cm in diameter [eluent: cyclohexane/ethyl acetate 70/30 by volume)], collecting 20-cm³ fractions. Fractions 3 to 8 are combined and concentrated to dryness under reduced pressure (2.7 kPa) at 40° C. 4.8 g of 2-methylcyclohexyl (1RS,2SR)-2-anilinoacetate are then obtained in the form of an oil which is used as such in the subsequent syntheses.

(1RS,2SR)-2-Methylcyclohexyl bromoacetate may be prepared in a manner analogous to that described in Example 2 for the preparation of 1-methylcyclopentyl bromoacetate, but using 6.8 g of (1RS,2SR)-2-methylcyclohexanol, 7.3 g of N,N-dimethylaniline and 5 g of bromoacetyl bromide as starting materials. The product obtained is purified by chromatography on 40 g of silica (0.06–0.200 mm) contained in a column 1.5 cm in diameter (eluent: dichloromethane), collecting 20-cm³ fractions. Fractions 2 to 4 are combined and concentrated to dryness under reduced pressure (2.7 kPa) at 40° C. 4.7 g of (1RS,2SR)-2-methylcyclohexyl bromoacetate are then obtained in the form of an oil which is used as such in the subsequent syntheses.

Example 4

The procedure is carried out in a manner analogous to that described in Example 1, but using 3.0 g of 1-methylcyclohexyl 2-anilinoacetate, 2.5 g of 2-[3-(3-methylphenyl)ureido]acetic acid and 0.9 cm³ of thionyl chloride as starting materials. The product obtained is purified by chromatography on 40 g of silica (0.063–0.200 mm) contained in a column 1.5 cm in diameter [eluent: cyclohexane/ethyl acetate (70/30 by volume)], collecting 20-cm³ fractions. Fractions 3 to 8 are combined and concentrated to dryness under reduced pressure (2.7 kPa) at 40° C. After-recrystallization from an acetonitrile/diisopropyl ether mixture (50/50 by volume), 0.6 g of 1-methylcyclohexyl 2-{2-[3-(3-methylphenyl)ureido]-N-phenylacetamido}acetate melting at 192° C. is obtained.

1-Methylcyclohexyl 2-anilinoacetate may be prepared in a manner analogous to that described in Example 1 for the preparation of 1,1,1,3,3,3-hexafluoro-2-propyl (RS)-2-anilino-2-phenylacetate, but using 3.8 g of 1-methylcyclohexyl bromoacetate and 3.0 g of aniline as starting materials. The product obtained is purified by chromatography on 80 g of silica (0.063–0.200 mm) contained in a column 2 cm in diameter [eluent: cyclohexane/ethyl acetate (70/30 by volume)], collecting 20-cm³ fractions. Fractions 2 to 6 are combined and concentrated to dryness under reduced pressure (2.7 kPa) at 40° C. 3.0 g of 1-methylcyclohexyl 2-anilinoacetate are then obtained in the form of an oil which is used as such in the subsequent syntheses.

1-Methylcyclohexyl bromoacetate may be prepared in a manner analogous to that described in Example 2 for the preparation of 1-methylcyclopentyl bromoacetate, but using 6.8 g of 1-methylcyclohexanol, 7.3 g of N,N-dimethylaniline and 5.0 g of bromoacetyl bromide as starting materials. The product obtained is purified by chromatography on 40 g of silica (0.063–0.200 mm) contained in a column 1.5 cm in diameter (eluent: dichloromethane), collecting 20-cm³ fractions. Fractions 2 to 5 are combined and concentrated to dryness under reduced pressure (2.7 kPa) at 40° C. 3.8 g of 1-methylcyclohexyl bromoacetate are then obtained in the form of an oil which is used as such in the subsequent syntheses.

Example 5

The procedure is carried out in a manner analogous to that described in Example 1, but using 3.3 g of cinnamyl 2-anilinoacetate, 2.6 g of 2-[3-(3-methylphenyl)ureido]acetic acid and 0.9 cm³ of thionyl chloride as starting materials. The product obtained is purified by chromatography on 60 g of silica (0.063–0.200 mm) contained in a column 2.0 cm in diameter [eluent: cyclohexane/ethyl acetate (50/50 by volume)], collecting 20-cm³ fractions. Fractions 4 to 8 are combined and concentrated to dryness under reduced pressure (2.7 kPa) at 40° C. After recrystallization from acetonitrile, 1.4 g of cinnamyl 2-{2-[3-(3-methylphenyl)ureido]-N-phenylacetamido}acetate melting at 158° C. are obtained.

Cinnamyl 2-anilinoacetate may be prepared in a manner analogous to that described in Example 1 for the preparation of 1,1,1,3,3,3-hexafluoro-2-propyl (RS)-2-anilino-2-phenylacetate, but using 3.8 g of cinnamyl bromoacetate and 2.8 g of aniline as starting materials. The product obtained is purified by chromatography on 50 g of silica (0.063–0.200 mm) contained in a column 2.0 cm in diameter [eluent: cyclohexane/ethyl acetate (70/30 by volume)], collecting 20-cm³ fractions. Fractions 3 to 6 are combined and concentrated to dryness under reduced pressure (2.7 kPa) at 40° C. 3.4 g of cinnamyl 2-anilinoacetate are then obtained in the form of an oil which is used as such in the subsequent syntheses.

Cinnamyl bromoacetate may be prepared in a manner analogous to that described in Example 1 for the preparation of 1,1,1,3,3,3-hexafluoro-2-propyl (RS)-α-bromophenylacetate, but using 3.9 g of cinnamyl alcohol, 2.7 g of triethylamine and 5.0 g of bromoacetyl bromide as starting materials. 3.3 g of cinnamyl bromoacetate are then obtained in the form of an oil which is used as such in the subsequent syntheses.

Example 6

The procedure is carried out in a manner analogous to that described in Example 1, but using 2.3 g of 2,2,2-trifluoroethyl 2-anilinoacetate, 2.1 g of 2-[3-(3-methylphenyl)ureido]acetic acid and 0.7 cm³ of thionyl chloride as starting materials. The product obtained is purified by chromatography on 40 g of silica (0.063–0.200 mm) contained in a column 1.5 cm in diameter [eluent: methylene chloride/ethanol (98/2 by volume)], collecting 10-cm³ fractions. Fractions 5 to 8 are combined and concentrated to dryness under reduced pressure (2.7 kPa) at 40° C. After recrystallization from diisopropyl ether, 0.6 g of 2,2,2-trifluoroethyl 2-{2-[3-(3-methylphenyl)ureido]-N-phenylacetamido}acetate melting at 172° C. is obtained.

2,2,2-Trifluoroethyl 2-anilinoacetate may be prepared in a manner analogous to that described in Example 1 for the preparation of 1,1,1,3,3,3-hexafluoro-2-propyl (RS)-2-anilino-2-phenylacetate, but using 3.5 g of 2,2,2-trifluoroethyl bromoacetate and 2.9 g of aniline as starting materials. The product obtained is purified by chromatography on 50 g of silica (0.063–0.200 mm) contained in a column 2 cm in diameter [eluent: cyclohexane/ethyl acetate (50/50 by volume)], collecting 20-cm³ fractions. Fractions 3 to 5 are combined and concentrated to dryness under reduced pressure (2.7 kPa) at 40° C. 2.3 g of 2,2,2-trifluoroethyl 2-anilinoacetate are then obtained in the form of a paste which is used as such in the subsequent syntheses.

2,2,2-Trifluoroethyl bromoacetate may be prepared in a manner analogous to that described in Example 1 for the preparation of 1,1,1,3,3,3-hexafluoro-2-propyl (RS)-α-bromophenylacetate, but using 2.5 g of 2,2,2-trifluoroethanol, 2.7 g of triethylamine and 5.0 g of bromoacetyl bromide as starting materials. 2.9 g of 2,2,2-trifluoroethyl bromoacetate are then obtained in the form of an oil which is used as such in the subsequent syntheses.

Example 7

The procedure is carried out in a manner analogous to that described in Example 1, but using 1.7 g of 3-pentyl 2-anilinoacetate, 1.5 g of 2-[3-(3-methylphenyl)ureido]acetic acid and 0.9 g of thionyl chloride as starting materials. The product obtained is purified by chromatography on 100 g of silica (0,063–0,200 mm) contained in a column 2.5 cm in diameter [eluent: cyclohexane/ethyl acetate (70/30 by volume)], collecting 30-cm$^3$ fractions. Fractions 19 to 32 are combined and concentrated to dryness under reduced pressure (2.7 kPa) at 40° C. After recrystallization from diisopropyl ether, 0.5 g of 3-pentyl 2-{2-[3-(3-methylphenyl)ureido]-N-phenylacetamido}acetate melting at 118° C. is obtained.

3-Pentyl 2-anilinoacetate may be prepared in a manner analogous to that described in Example 1 for the preparation of 1,1,1,3,3,3-hexafluoro-2-propyl (RS)-2-anilino-2-phenylacetate, but using 5.0 g of 3-pentyl bromoacetate and 4.5 g of aniline as starting materials. The product obtained is purified by chromatography on 100 g of silica (0.063–0.200 mm) contained in a column 3.5 cm in diameter (eluent: dichloromethane), collecting 50-cm$^3$ fractions. Fractions 5 to 13 are combined and concentrated to dryness under reduced pressure (2.7 kPa) at 40° C. 8.6 g of 3-pentyl 2-anilinoacetate are then obtained in the form of an oil which is used as such in the subsequent syntheses.

3-Pentyl bromoacetate may be prepared in a manner analogous to that described in Example 1 for the preparation of 1,1,1,3,3,3-hexafluoro-2-propyl (RS)-α-bromophenylacetate, but using 3.8 g of pentan-3-ol, 4.7 g of triethylamine and 8.5 g of bromoacetyl bromide as starting materials. 5.0 g of 3-pentyl bromoacetate are then obtained in the form of an oil which is used as such in the subsequent syntheses.

Example 8

The procedure is as in Example 1, but 2.1 g of 2-[3-(3-methylphenyl)ureido]acetic acid, 3.14 g of tert-butyl (RS)-2-anilino-2-(4-methoxyphenyl)acetate and 0.72 cm$^3$ of thionyl chloride are used as starting materials. The residue obtained is purified by chromatography on 100 g of silica (0.04–0.063 mm) contained in a column 3 cm in diameter [eluent: cyclohexane/ethyl acetate (70/30 by volume)], using an excess pressure of 40 kPa of nitrogen and collecting 10-cm$^3$ fractions. Fractions 12 to 18 are combined and concentrated to dryness under reduced pressure (2.7 kPa) at 40° C. and the residue obtained is recrystallized from a mixture of diisopropyl ether/acetonitrile (50/50 by volume). 2.3 g of tert-butyl (RS)-2-(4-methoxyphenyl)-2-{2-[3-(3-methylphenyl)ureido]-N-phenylacetamido}acetate melting at 206° C. are then obtained.

tert-Butyl (RS)-2-anilino-2-(4-methoxyphenyl)acetate may be prepared in the following way: 12.1 cm$^3$ of aniline are added to a solution of 20 g of tert-butyl (RS)-2-bromo-2-(4-methoxyphenyl)acetate in 100 cm$^3$ of acetonitrile and the reaction mixture is kept under reflux for 5 hours and then for 20 hours at a temperature close to 20° C. The insoluble product is separated off by filtration and the filtrate is concentrated to dryness under reduced pressure (2.7 kPa). The product obtained is purified by chromatography on 250 g of silica (0.04–0.063 mm) contained in a column 4.2 cm in diameter (eluent: ethyl acetate/cyclohexane (10/90 by volume)], using an excess pressure of 40 kPa of nitrogen and collecting 10-cm$^3$ fractions. Fractions 6 to 17 are combined and concentrated to dryness under reduced pressure (2.7 kPa) at 40° C. and the residue obtained is crystallized from 150 cm$^3$ of petroleum ether. 12 g of tert-butyl (RS)-2-anilino-2-(4-methoxyphenyl)acetate melting at 99° C. are then obtained.

tert-Butyl (RS)-2-bromo-2-(4-methoxyphenyl)acetate may be prepared in the following way: 13.2 g of N-bromosuccinimide and 0.1 g of azobisisobutyronitrile are added to a suspension of 15 g of tert-butyl 2-(4-methoxyphenyl)acetate in 74 cm$^3$ of carbon tetrachloride. The reaction mixture is kept under reflux for 8 hours and then at a temperature close to 20° C. for 20 hours. The insoluble product is separated off by filtration and the filtrate is concentrated to dryness under reduced pressure (2.7 kPa). 20 g of tert-butyl (RS)-2-bromo-2-(4-methoxyphenyl)acetate are then obtained in the form of an oil which is used as such in the subsequent syntheses.

tert-Butyl 2-(4-methoxyphenyl)acetate may be prepared in the following way: 18 g of 2-(4-methoxyphenyl)acetyl chloride are added to a solution of 31 cm$^3$ of N,N-dimethylaniline in 41.3 cm$^3$ of tert-butanol. The mixture is stirred for 20 hours at a temperature close to 20° C. and then poured into 400 cm$^3$ of diethyl ether and 200 cm$^3$ of water. The organic phase is separated off, washed with 3 times 200 cm$^3$ of water, 3 times 200 cm$^3$ of a 2N aqueous hydrochloric acid solution and finally with 3 times 200 cm$^3$ of water, then dried over magnesium sulphate and concentrated to dryness under reduced pressure (2.7 kPa). The product obtained is purified by chromatography on 350 g of silica (0.04–0.063 mm) contained in a column 7 cm in diameter [eluent: ethyl acetate/cyclohexane (10/90 by volume)], using an excess pressure of 40 kPa of nitrogen and collecting 10-cm$^3$ fractions. Fractions 1 to 18 are combined and concentrated to dryness under reduced pressure (2.7 kPa) at 40° C. 15 g of tert-butyl 2-(4-methoxyphenyl)acetate are then obtained in the form of an oil which is used as such in the subsequent syntheses.

2-(4-Methoxyphenyl)acetyl chloride may be prepared by the method described by H. Yamaguchi, Yakugaku Zasski, 78, 733 (1958).

Example 9

The procedure is as in Example 8, but using 2.1 g of 2-[3-(3-methylphenyl)ureido]acetic acid, 3.18 g of tert-butyl (RS)-2-anilino-2-(4-chlorophenyl)acetate and 0.72 cm$^3$ of thionyl chloride as starting materials. The product obtained is purified by chromatography on 250 g of silica (0.04–0.063 mm) contained in a column 4.2 cm in diameter [eluent: ethyl acetate/cyclohexane (30/70 by volume)], using an excess pressure of 40 kPa of nitrogen and collecting 10-cm$^3$ fractions. Fractions 8 to 17 are combined and concentrated to dryness under reduced pressure (2.7 kPa) at 40° C. and the residue obtained is recrystallized from diisopropyl ether. 2.6 g of tertbutyl (RS)-2-(4-chlorophenyl)-2-{2-[3-(3-methylphenyl- )ureido]-N-phenylacetamido}acetate melting at 167° C. are then obtained.

tert-Butyl (RS)-2-anilino-2-(4-chlorophenyl)acetate may be prepared in a manner analogous to that described in Example 8 for the preparation of tert-butyl (RS)-2-anilino-2-(4-methoxyphenyl)acetate, but using 15.3 g of tert-butyl (RS)-2-bromo-2-(4-chlorophenyl)acetate chlorophenyl)acetate and 9.1 cm³ of aniline in 150 cm³ of acetonitrile as starting materials. 5.2 g of tert-butyl (RS)-2-anilino-2-(4-chlorophenyl)acetate melting at 98° C. are then obtained.

tert-Butyl (RS)-2-bromo-2-(4-chlorophenyl)acetate may be prepared in the following way: 40 g of (RS)-2-bromo-2-(4-chlorophenyl)acetyl chloride are added in the course of 1 hour to a solution of 63 cm³ of tert-butanol and 46.9 cm³ of N,N-dimethylaniline. The mixture is kept at a temperature close to 20° C. for 20 hours and then poured into 400 cm³ of diethyl ether and 200 cm³ of water. The organic phase is separated off, washed with 3 times 200 cm³ of water, 3 times 200 cm³ of a 2N aqueous hydrochloric acid solution and finally with 3 times 200 cm³ of water, then dried over magnesium sulphate and concentrated to dryness under reduced pressure (2.7 kPa). 32.5 g of tert-butyl (RS)-2-bromo-2-(4-chlorophenyl)acetate are then obtained in the form of an oil which is used as such in the subsequent syntheses.

(RS)-2-Bromo-2-(4-chlorophenyl)acetyl chloride may be prepared in the following way: a solution of 25.6 g of 2-(4-chlorophenyl)acetic acid and 18.6 g of thionyl chloride is stirred for 3 hours under reflux until the evolution of gas ceases. The mixture is cooled to a temperature close to 30° C. 8.45 cm³ of bromine are added and the mixture is then refluxed for 5 hours. The reaction mixture is concentrated to dryness under reduced pressure (2.7 kPa) at 45° C. 40 g of (RS)-2-bromo-2-(4-chlorophenyl)acetyl chloride are then obtained, which is used as such for the following step.

Example 10

The procedure is as in Example 1, but 2.1 g of 2-[3-(3-methylphenyl)ureido]acetic acid, 3.52 g of tert-butyl (RS)-2-anilino-2-(3,4-dichlorophenyl)acetate and 0.72 cm³ of thionyl chloride are used as starting materials. The product obtained is purified by chromatography on 100 g of silica (0.04–0.063 mm) contained in a column 3 cm in diameter [eluent: ethyl acetate/cyclohexane (30/70 by volume)], using an excess pressure of 40 kPa of nitrogen and collecting 10-cm³ fractions. Fractions 13 to 24 are combined and concentrated to dryness under reduced pressure (2.7 kPa) at 40° C. and the residue obtained is recrystallized from diisopropyl ether. 2.6 g of tert-butyl (RS)-2-(3,4-dichlorophenyl)-2-{2-[3-(3-methylphenyl)ureido]-N-phenylacetamido}acetate melting at 176° C. are then obtained.

tert-Butyl (RS)-2-anilino-2-(3,4-dichlorophenyl)acetate may be prepared in a manner analogous to that described in Example 8 for the preparation of tert-butyl (RS)-2-anilino-2-(4-methoxyphenyl)acetate, but using 17 g of tert-butyl (RS)-2-bromo-2-(3,4-dichlorophenyl)acetate and 9.1 cm³ of aniline in 100 cm³ of acetonitrile as starting materials. 9.0 g of tert-butyl (RS)-2-anilino-2-(3,4-dichlorophenyl)acetate melting at 94° C. are then obtained.

tert-Butyl (RS)-2-bromo-2-(3,4-dichlorophenyl)acetate may be prepared in a manner analogous to that described in Example 9 for the preparation of tert-butyl (RS)-2-bromo-2-(4-chlorophenyl)acetate, but using 38 g of (RS)-2-bromo-2-(3,4-dichlorophenyl)acetyl chloride, 53.2 cm³ of tert-butanol and 39.7 cm³ of N,N-dimethylaniline as starting materials. The product obtained is purified by chromatography on 250 g of silica (0.04–0.063 mm) contained in a column 4.2 cm in diameter [eluent: ethyl acetate/cyclohexane (10/90 by volume)], using an excess pressure of 40 kPa of nitrogen and collecting 10-cm³ fractions. Fractions 5 to 12 are combined and concentrated to dryness under reduced pressure (2.7 kPa) at 40° C. By crystallization of the residue obtained from 200 cm³ of petroleum ether, 20 g of tert-butyl (RS)-2-bromo-2-(3,4-dichlorophenyl)acetate melting at 88° C. are obtained.

(RS)-2-Bromo-2-(3,4-dichlorophenyl)acetyl chloride may be prepared by the manner described in Example 9 for the preparation of (RS)-2-bromo-2-(4-chlorophenyl)acetyl chloride, but using 25 g of 2-(3,4-dichlorophenyl)acetic acid, 14.9 cm³ of thionyl chloride and 7.7 cm³ of bromine as starting materials. 38 g of (RS)-2-bromo-2-(3,4-dichlorophenyl)acetyl chloride are then obtained, which is used as such for the following step.

Example 11

The procedure is as in Example 1, but using 4.19 g of 2-[3-(3-methylphenyl)ureido]acetic acid, 6.57 g of tert-butyl (RS)-2-anilino-2-(4-nitrophenyl)acetate in 100 cm³ of anhydrous 1,2-dichloroethane and 1.42 cm³ of thionyl chloride as starting materials. The product obtained is purified by chromatography on 250 g of silica (0.04–0.063 mm) contained in a column 4.2 cm in diameter [eluent: ethyl acetate/cyclohexane (30/70 by volume)], using an excess pressure of 40 kPa of nitrogen and collecting 10-cm³ fractions. Fractions 25 to 39 are combined and concentrated to dryness under reduced pressure (2.7 kPa) at 40° C. and the residue obtained is recrystallized from acetonitrile. 3 g of tert-butyl (RS)-2-{2-[3-(3-methylphenyl)ureido]-Nphenylacetamido}2-(4-nitrophenyl)acetate melting at 212° C. are then obtained.

tert-Butyl (RS)-2-anilino-2-(4-nitrophenyl)acetate may be prepared in a manner analogous to that described in Example 8 for the preparation of tert-butyl (RS)-2-anilino-2-(4-methoxyphenyl)acetate, but using 23.7 g of tert-butyl (RS)-2-bromo-2-(4-nitrophenyl)acetate and 13.7 cm³ of aniline in 100 cm³ of acetonitrile as starting materials. The product obtained is purified by chromatography on 250 g of silica (0.04–0.063 mm) contained in a column 4.2 cm in diameter [eluent: ethyl acetate/cyclohexane (20/80 by volume)], using an excess pressure of 40 kPa of nitrogen and collecting 20-cm³ fractions. Fractions 10 to 18 are combined and concentrated to dryness under reduced pressure (2.7 kPa) at 40° C. 15 g of tert-butyl (RS)-2-anilino-2-(4-nitrophenyl)acetate are then obtained in the form of an oil which is used as such in the subsequent syntheses.

tert-Butyl (RS)-2-bromo-2-(4-nitrophenyl)acetate may be prepared in a manner analogous to that described in Example 8 for the preparation of tert-butyl (RS)-2-bromo-2-(4-chlorophenyl)acetate, but using 56 g of (RS)-2-(4-nitrophenyl)bromoacetyl chloride, 84.7 cm³ of tert-butanol and 63 cm³ of N,N-dimethylaniline as starting materials. The product obtained is purified by chromatography on 250 g of silica (0.04–0.063 mm) contained in a column 4.2 cm in diameter [eluent: ethyl acetate/cyclohexane (10/90 by volume)], using an excess pressure of 40 kPa of nitrogen and collecting 20-cm³ fractions. Fractions 7 to 20 are combined and concentrated to dryness under reduced pressure (2.7 kPa) at 40° C. 37 g of tert-butyl (RS)-2-bromo-2-(4-nitrophenyl)acetate are then obtained in the form of an oil which is used as such in the subsequent syntheses.

(RS)-2-bromo-2-(4-nitrophenyl)acetyl chloride may be prepared by the method described in Example 9 for the preparation of (RS)-2-bromo-2-(4-chlorophenyl)acetyl chloride, but using 36.2 g of 2-(4-nitrophenyl)acetic acid, 24.4 cm³ of thionyl chloride and 12.7 cm³ of bromine as starting materials. 56 g of (RS)-2-bromo-2-(4-nitrophenyl)acetyl chloride are then obtained, which is used as such for the following step.

Example 12

0.68 g of iron powder and 0.5 cm³ of concentrated hydrochloric acid are added to a suspension of 2.1 g of tert-butyl (RS)-2-{2-[3-(3methylphenyl)ureido]-N-phenylacetamido}-2-(4-nitrophenyl)acetate in 40 cm³ of a mixture of ethanol and water (50/50 by volume) heated under reflux. The reaction mixture is kept under reflux for 4 hours and after cooling it is rendered alkaline to pH 8 using a saturated aqueous sodium bicarbonate solution. The insoluble product is removed by filtration and the filtrate is extracted with 3 times 100 cm³ of dichloromethane. The organic extracts are washed with twice 100 cm³ of water, dried over magnesium sulphate and concentrated to dryness under reduced pressure (2.7 kPa) at 40° C. The oily residue obtained is purified by chromatography on 100 g of silica (0.04–0.063 mm) contained in a column 3 cm in diameter [eluent: methanol/dichloromethane (1/99 by volume)], using an excess pressure of 40 kPa of nitrogen and collecting 10-cm³ fractions. Fractions 8 to 14 are combined and concentrated to dryness under reduced pressure (2.7 kPa) at 40° C. After recrystallization from isopropyl ether, 0.8 g of tert-butyl (RS)-2-(4-aminophenyl)-2-{2-[3-(3-methylphenyl)ureido]-N-phenylacetamido}acetate melting at 108° C. is obtained.

Example 13

The procedure is as in Example 1, but using 2.1 g of 2-[3-(3-methylphenyl)ureido]acetic acid, 3.18 g of tert-butyl (RS)-2-anilino-2-(3-chlorophenyl)acetate and 0.72 cm³ of thionyl chloride as starting materials. The product is purified by chromatography on 100 g of silica (0.04–0,063 mm) contained in a column 3 cm in diameter [eluent: ethyl acetate/cyclohexane (30/70 by volume)], using an excess pressure of 40 kPa of nitrogen and collecting 10-cm³ fractions. Fractions 10 to 20 are combined and concentrated to dryness under reduced pressure (2.7 kPa) at 40° C. and the residue obtained is re-crystallized from a mixture of isopropyl ether/cyclohexane (50/50 by volume) to give 2.1 g of a solid which is repurified by chromatography on 100 g of silica (0.04–0.063 mm) contained in a column 3 cm in diameter [eluent: dichloromethane/methanol (99/1 by volume)], using an excess pressure of 40 kPa of nitrogen and collecting 10-cm³ fractions. Fractions 11 to 26 are combined and concentrated to dryness under reduced pressure (2.7 kPa) at 40° C. and the residue obtained is recrystallized from a toluene/cyclohexane mixture (20/80 by volume). 1.7 g of tert-butyl (RS)-2-(3-chlorophenyl)-2-{2-[3-(3-methylphenyl)ureido]-N-phenylacetamido}acetate melting at 100° C. are then obtained.

tert-Butyl (RS)-2-anilino-2-(3-chlorophenyl)acetate may be prepared in a manner analogous to that described in Example 8 for the preparation of tert-butyl (RS)-2-anilino-2-(4-methoxyphenyl)acetate, but using 15.3 g of tert-butyl (RS)-2-bromo-2-(3-chlorophenyl)acetate and 9.2 cm³ of aniline in 100 cm³ of acetonitrile as starting materials. 4.8 g of tert-butyl (RS)-2-anilino-2-(3-chlorophenyl)acetate melting at 96° C. are then obtained.

tert-Butyl (RS)-2-bromo-2-(3-chlorophenyl)acetate may be prepared in a manner analogous to that described in Example 9 for the preparation of tert-butyl (RS)-2-bromo-2-(4-chlorophenyl)acetate, but using 31 g of (RS)-2-(3-chlorophenyl)bromoacetyl chloride, 49.1 cm³ of tert-butanol and 36.5 cm³ of N,N-dimethylaniline as starting materials. The product obtained is purified by chromatography on 250 g of silica (0.04–0.063 mm) contained in a column 4.2 cm in diameter [eluent: ethyl acetate/cyclohexane (10/90 by volume)], using an excess pressure of 40 kPa of nitrogen and collecting 20-cm³ fractions. Fractions 6 to 16 are combined and concentrated to dryness under reduced pressure (2.7 kPa) at 40° C. 21 g of tert-butyl (RS)-2-bromo-2-(3-chlorophenyl)acetate are then obtained in the form of an oil which is used as such in the subsequent syntheses.

(RS)-2-bromo-2-(3-chlorophenyl)acetyl chloride may be prepared by the method described in Example 9 for the preparation of (RS)-2-bromo-2-(4-chlorophenyl)acetyl chloride, but using 20 g of 2-(3-chlorophenyl)acetic acid, 14.3 cm³ of thionyl chloride and 7.4 cm³ of bromine as starting materials. 31 g of (RS)-2-bromo-2-(3-chlorophenyl)acetyl chloride are then obtained, which is used as such for the following step.

Example 14

The procedure is as in Example 1, but using 2.1 g of 2-[3-(3-methylphenyl)ureido]acetic acid, 3.2 g of tert-butyl (RS)-2-anilino-2-(2-chlorophenyl)acetate and 0.72 cm³ of thionyl chloride as starting materials. The product obtained is purified by chromatography on 100 g of silica (0.04–0.063 mm) contained in a column 3 cm in diameter [eluent: dichloromethane/methanol (99/1 by volume)], using an excess pressure of 40 kPa of nitrogen and collecting 10-cm³ fractions. Fractions 7 to 15 are combined and concentrated to dryness under reduced pressure (2.7 kPa) at 40° C. and the residue obtained is recrystallized from a mixture of acetonitrile and isopropyl ether (10/90 by volume). 2 g of tert-butyl (RS)-2-(2-chlorophenyl)-2-{2-[3-(3-methylphenyl)ureido]-N-phenylacetamido}acetate melting at 181° C. are then obtained.

tert-Butyl (RS)-2-anilino-2-(2-chlorophenyl)acetate may be prepared in a manner analogous to that described in Example 8 for the preparation of tert-butyl (RS)-2-anilino-2-(4-methoxyphenyl)acetate, but using 15.3 g of tert-butyl (RS)-2-bromo-2-(2-chlorophenyl)acetate and 9.2 cm³ of aniline in 75 cm³ of acetonitrile as starting materials. 7 g of tert-butyl (RS)-2-anilino-2-(2-chlorophenyl)acetate melting at 74° C. are then obtained.

tert-Butyl (RS)-2-bromo-2-(2-chlorophenyl)acetate may be prepared in a manner analogous to that described in Example 9 for the preparation of tert-butyl (RS)-2-bromo-2-(4-chlorophenyl)acetate, but using 39 g of (RS)-2-bromo-2-(2-chlorophenyl)acetyl chloride and 61.6 cm³ of tert-butanol and 45.8 cm³ of N,N-dimethylaniline as starting materials. The product obtained is purified by chromatography on 250 g of silica (0.04–0.063 mm) contained in a column 4.2 cm in diameter [eluent: ethyl acetate/cyclohexane (10/90 by volume)], using an excess pressure of 40 kPa of nitrogen and collecting 10-cm³ fractions. Fractions 4 to 15 are combined and concentrated to dryness under reduced pressure (2.7 kPa) at 40° C. 28.5 g of tert-butyl (RS)-2-bromo-2-(2-chlorophenyl)acetate are then obtained in the form of an oil which is used as such in the subsequent syntheses.

(RS)-2-bromo-2-(2-chlorophenyl)acetyl chloride may be prepared by the method described in Example 9 for the preparation of (RS)-2-bromo-2-(4-chlorophenyl)acetyl chloride, but using 25 g of 2-(2-chlorophenyl)acetic acid, 7.8 cm³ of thionyl chloride and 9.3 cm³ of bromine as starting materials. 39 g of (RS)-2-bromo-2-(2-chlorophenyl)acetyl chloride are then obtained, which is used as such for the following step.

Example 15

The procedure is as in Example 1, but using 1.04 g of 2-[3-(3-methylphenyl)ureido]acetic acid, 1.8 g of tert-butyl (RS)-2-anilino-2-(3-bromophenyl)acetate and 0.36 cm³ of thionyl chloride as starting materials The product obtained is purified by chromatography on 100 g of silica (0.04–0.063 mm) contained in a column 3 cm in diameter [eluent: methanol/dichloromethane (1/99 by volume)], using an excess pressure of 40 kPa of nitrogen and collecting 10-cm³ fractions. Fractions 11 to 17 are combined and concentrated to dryness under reduced pressure (2.7 kPa) at 40° C. and the residue obtained is recrystallized from cyclohexane. 1.4 g of tert-butyl (RS)-2-(3-bromophenyl)-2-{2-[3-(3-methylphenyl)ureido]-N-phenylacetamido}acetate melting at 103° C. are then obtained.

tert-Butyl (RS)-2-anilino-2-(3-bromophenyl)acetate may be prepared in a manner analogous to that described in Example 8 for the preparation of tert-butyl (RS)-2-anilino-2-(4-methoxyphenyl)acetate, but using 6 g of tert-butyl (RS)-2-bromo-2-(3-bromophenyl)acetate and 3.2 cm³ of aniline in 50 cm³ of acetonitrile as starting materials. 1.8 g of tert-butyl (RS)-2-anilino-2-(3-bromophenyl)acetate melting at 90° C. are then obtained.

tert-Butyl (RS)-2-bromo-2-(3-bromophenyl)acetate may be prepared in a manner analogous to that described in Example 9 for the preparation of tert-butyl (RS)-2-bromo-2-(4-chlorophenyl)acetate, but using 7 g of (RS)-2-(3-bromophenyl)bromoacetyl chloride, 9.5 cm³ of tert-butanol and 7.1 cm³ of N,N-dimethylaniline as starting materials. The product obtained is purified by chromatography on 100 g of silica (0.04–0.063 mm) contained in a column 3 cm in diameter [eluent: ethyl acetate/cyclohexane (10/90 by volume)], using an excess pressure of 40 kPa of nitrogen and collecting 10-cm³ fractions. Fractions 5 to 16 are combined and concentrated to dryness under reduced pressure (2.7 kPa) at 40° C. 6 g of tert-butyl (RS)-2-bromo-2-(3-bromophenyl)acetate are then obtained in the form of an oil which is used as such in the subsequent syntheses.

(RS)-2-Bromo-2-(3-bromophenyl)acetyl chloride may be prepared by the method described in Example 9 for the preparation of (RS)-2-bromo-2-(4-chlorophenyl)acetyl chloride, but using 5 g of 2-(3-bromophenyl)acetic acid, 2.8 cm³ of thionyl chloride and 1.5 cm³ of bromine as starting materials. 7 g of (RS)-2-bromo-2-(3-chlorophenyl)acetyl chloride are then obtained, which is used as such for the following step.

Example 16

The procedure is as in Example 1, but using 2.1 g of 2-[3-(3-methylphenyl)ureido]acetic acid, 3.02 g of tert-butyl (RS)-2-anilino-2-(3-fluorophenyl)acetate and 0.72 cm³ of thionyl chloride as starting materials. The product obtained is purified by chromatography on 100 g of silica (0.04–0.063 mm) contained in a column 3 cm in diameter [eluent: methanol/dichloromethane (1/99 by volume)], using an excess pressure of 40 kPa of nitrogen and collecting 10-cm³ fractions. Fractions 10 to 16 are combined and concentrated to dryness under reduced pressure (2.7 kPa) at 40° C. and the residue obtained is recrystallized from cyclohexane. 1.3 g of tert-buty (RS)-2-(3-fluorophenyl)-2-{2-[3-(3-methylphenyl)ureido]-N-phenylacetamido}acetate melting at 107° C. are then obtained.

tert-Butyl (RS)-2-anilino-2-(3-fluorophenyl)acetate may be prepared in a manner analogous to that described in Example 8 for the preparation of tert-butyl (RS)-2-anilino-2-(4-methoxyphenyl)acetate, but using 11 g of tert-butyl (RS)-2-bromo-2-(3-fluorophenyl)acetate and 7 cm³ of aniline in 100 cm³ of acetonitrile as starting materials. 5.7 g of tert-butyl (RS)-2-anilino-2-(3-fluorophenyl)acetate melting at 90° C. are then obtained.

tert-Butyl (RS)-2-bromo-2-(3-fluorophenyl)acetate may be prepared in a manner analogous to that described in Example 9 for the preparation of tert-butyl (RS)-2-bromo-2-(4-chlorophenyl)acetate, but using 15.5 g of (RS)-2-(3-fluorophenyl)bromoacetyl chloride, chloride, 26.1 cm³ of tert-butanol and 19.4 cm³ of N,N-dimethylaniline as starting materials. The product obtained is purified by chromatography on 250 g of silica (0.04–0.063 mm) contained in a column 4.2 cm in diameter [eluent: ethyl acetate/cyclohexane (10/90 by volume)], using an excess pressure of 40 kPa of nitrogen and collecting 10-cm³ fractions. Fractions 7 to 14 are combined and concentrated to dryness under reduced pressure (2.7 kPa) at 40° C. 11 g of tert-butyl (RS)-2-bromo-2-(3-fluorophenyl)acetate are then obtained in the form of an oil which is used as such in the subsequent syntheses.

Example 17

The procedure is as in Example 1, but using 11.6 g of 2-[3-(3-methylphenyl)ureido]acetic acid, 15 g of ethyl (RS)-3-anilino-3-phenylpropionate and 4 cm³ of thionyl chloride as starting materials. The product obtained is purified by chromatography on 250 g of silica (0.04–0.063 mm) contained in a column 5 cm in diameter [eluent: methanol/dichloromethane (2/98 by volume)], using an excess pressure of 40 kPa of nitrogen and collecting 75-cm³ fractions. Fractions 19 to 21 are combined and concentrated to dryness under reduced pressure (2.7 kPa) at 40° C. and the residue obtained is recrystallized from ethyl acetate. 4.5 g of ethyl (RS)-3-{2-[3-(3-methylphenyl)ureido]-N-phenylacetamido}-3-phenylpropionate melting at 146° C. are then obtained.

Ethyl (RS)-3-anilino-3-phenylpropionate may be prepared in the following way: 12.4 cm³ of trifluoroacetic acid are added to a solution of 22.3 g of ethyl 3-anilino-3-phenylacrylate in 400 cm³ of anhydrous tetrahydrofuran, kept at a temperature close to 0° C., and a solution of 10.4 g of sodium cyanoborohydride in 60 cm³ of methanol is then introduced in the course of 20 minutes, with stirring. The reaction mixture is kept at a temperature close to 0° C. for 30 minutes and is then poured into 400 cm³ of a saturated aqueous sodium bicarbonate solution diluted with 500 cm³ of water. The aqueous phase is extracted with 3 times 150 cm³ of ethyl acetate and the organic extracts are washed with 30 times 200 cm³ of water, dried over magnesium sulphate and concentrated to dryness under reduced pressure (2.7 kPa) at 45° C. 14.1 g of ethyl (RS)-3-anilino-3-phenylpropionate melting at 87° C. are then obtained.

Ethyl 3-anilino-3-phenylacrylate may be prepared by the method described by F. Texier-Boullet., Synthesis, (1985), 679.

Example 18

1 g of triethylamine and 0.49 g of trichloromethyl chloroformate are added, at a temperature close to 0° C., to a solution of 0.72 g of 3-aminoquinoline in 30 cm³ of dichloromethane. The suspension obtained is stirred for 15 minutes at a temperature close to 0° C. and a solution of 1.3 g of tert-butyl 2-(2-amino-N-phenylacetamido)acetate in 10 cm³ of dichloromethane is then added. The reaction mixture is stirred for 3 hours at a temperature close to 20° C. and 20 cm³ of water are then added. The aqueous phase is separated off by decantation and then reextracted with twice 15 cm³ of 1,2-dichloroethane. The organic phases are combined, washed with twice 10 cm³ of water, dried over magnesium sulphate, filtered and then concentrated to dryness under reduced pressure (2.7 kPa) at 40° C. The oil obtained is purified by chromatography on 50 g of silica (0.063–0.2 mm) contained in a column 1.5 cm in diameter [eluent: dichloromethane/methanol (98/2 by volume)], collecting 10-cm³ fractions. The fractions containing only the desired product are combined and concentrated to dryness under reduced pressure (2.7 kPa) at 40° C. After recrystallization from ethyl acetate, 0.8 g of tert-butyl 2-{2-[3-(3-quinolyl)ureido]-N-phenylacetamido}acetate melting at 191° C. is obtained.

tert-Butyl 2-(2-amino-N-phenylacetamido)acetate may be prepared in the following way: 1.4 g of methylhydrazine are added, at a temperature close to 0° C., to a solution of 3.9 g of tert-butyl 2-(N-phenyl-2-phthalimidoacetamido)acetate in 70 cm³ of dichloromethane. The reaction mixture is stirred four 48 hours at a temperature close to 20° C., 50 cm³ of water are then added, the mixture is stirred and the aqueous phase is separated off by decanting and is reextracted with twice 40 cm³ of dichloromethane. The organic phases are combined, dried over magnesium sulphate, filtered and then concentrated to dryness under reduced pressure (2.7 kPa) at 40° C. The oil obtained is purified by chromatography on 80 g of silica (0.063–0.2 mm) contained in a column 2 cm in diameter [eluent: ethyl acetate/methanol (90/10 by volume)], collecting 20-cm³ fractions. The fractions containing only the desired product are combined and concentrated to dryness under reduced pressure (2.7 kPa) at 40° C. 3.8 g of tert-butyl 2-(2-amino-N-phenylacetamido)acetate are then obtained in the form of an oil which is used as such in the subsequent syntheses.

tert-Butyl 2-(N-phenyl-2-phthalimidoacetamido)acetate may be prepared in the following way: 42 g of sodium bicarbonate are added to a solution of 94.9 g of tert-butyl 2-anilinoacetate in 360 cm³ of 1,2-dichloroethane, kept under an atmosphere of argon, and a solution of 102.4 g of 2-phthalimidoacetyl chloride in 400 cm³ of 1,2-dichloroethane is then added dropwise at a temperature close to 20° C. The solution obtained is stirred for 4 hours at a temperature close to 60° C. and 600 cm³ of water are then added. The aqueous phase is separated off by decanting and then reextracted with twice 300 cm³ of 1,2-dichloroethane. The organic phases are combined, dried over magnesium sulphate, filtered and then concentrated to dryness under reduced pressure (2.7 kPa) at 40° C. After recrystallization from diisopropyl ether, 152 g of tert-butyl 2-(N-phenyl-2-phthalimidoacetamido)acetate melting at 120° C. are then obtained.

tert-Butyl 2-anilinoacetate may be prepared in the following way: 204.7 g of tert-butyl bromoacetate are added to a solution of 196 g of aniline in 2100 cm³ of acetonitrile. The solution obtained is stirred under reflux for 4 hours. After cooling, the insoluble product is separated off by filtration and washed with 3 times 150 cm³ of acetonitrile. The filtrates are combined and concentrated to dryness under reduced pressure (2.7 kPa) at 40° C. The residual oil is purified by distillation under reduced pressure (0.27 kPa). 133 g of tert-butyl 2-anilinoacetate are then obtained in the form of a colorless liquid which distills at 122° C. under a pressure of 0.27 kPa.

2-Phthalimidoacetyl chloride may be prepared by the method described by W. Grassmann et al., Ber., 83, 244 (1950).

Example 19

A solution of 0.85 g of N,N'-carbonyldiimidazole in 10 cm³ of anhydrous dichloromethane is added dropwise, at a temperature close to 20° C., to a solution of 0.87 g of 2-quinolinecarboxylic acid in 15 cm³ of anhydrous dichloromethane. The suspension obtained is stirred for 3 hours at a temperature close to 20° C. and a solution of 2.6 g of tert-butyl 2-(2-amino-N-phenylacetamido)acetate in 25 cm³ of anhydrous dichloromethane is then added. The reaction mixture is stirred for 16 hours at a temperature close to 20° C. and 50 cm³ of water are then added. The aqueous phase is separated off by decanting and then reextracted with twice 15 cm³ of 1,2-dichloroethane. The organic phases are combined, washed with twice 25 cm³ of a saturated aqueous sodium bicarbonate solution and then with twice 25 cm³ of distilled water, dried over magnesium sulphate, filtered and concentrated to dryness under reduced pressure (2.7 kPa) at 40° C. After recrystallization of the residual solid from a mixture of cyclohexane and ethyl acetate (90/10 by volume), 0.8 g of tert-butyl 2-(N-phenyl-2-quinolinecarboxamidoacetamido)acetate melting at 114° C. is obtained.

Example 20

0.3 g of triethylamine and 0.66 g of 1-benzotriazolyloxytris(dimethylamino)phosphonium hexafluorophosphonate are added to a suspension of 0.51 g of 2-{2-[3-(3-methylphenyl)ureido]-Nphenylacetamido}acetic acid and 0.26 g of 1,1,1,3,3,3-hexafluoropropan-2-ol in 30 cm³ of dichloromethane. The solution is stirred for 2 hours at a temperature close to 25° C. and then poured into 50 cm³ of a saturated aqueous sodium chloride solution. The organic phase is separated off and the aqueous phase is extracted with 3 times 80 cm³ of ethyl acetate. The combined organic phases were washed successively with twice 30 cm³ of a 2N aqueous hydrochloric acid solution, twice 30 cm³ of a saturated aqueous sodium bicarbonate solution and 50 cm³ of a saturated aqueous sodium chloride solution, dried over magnesium sulphate and concentrated to dryness under reduced pressure (2.7 kPa) at 40° C. The product obtained is purified by chromatography on 40 g of silica (0.063–0.200 mm) contained in a column 1.5 cm in diameter [eluent: cyclohexane/ethyl acetate (50/50 by volume)], collecting 20-cm³ fractions. Fractions 3 to 6 are combined and concentrated to dryness under reduced pressure (2.7 kPa) at 40° C. After recrystallization from diisopropyl ether, 0.6 g of 1,1,1,3,3,3-hexafluoro-2-propyl 2-{2-[3-(3-methylphenyl)ureido]-Nphenylacetamido}acetate melting at 112° C. is obtained.

2-{2-[3-(3-Methylphenyl)ureido]-N-phenylacetamido}acetic acid may be prepared in the following way: 7 g of trifluoroacetic acid are added to a solution of 3.3 g of tert-butyl 2-{2-[3-(3-methylphenyl)ureido]-N-phenylacetamido}acetate in 25 cm³ of dichloromethane. The solution obtained is refluxed for 4 hours and then concentrated to dryness under reduced pressure (2.7 kPa) at 40° C. After recrystallization from diisopropyl ether, 2 g of 2-{2-[3-(3-methylphenyl)ureido]-N-phenylacetamido}acetic acid are obtained.

Example 21

The procedure is as in Example 1, but 0.85 g of 2-[3-(3-methylphenyl)ureido]acetic acid, 1.25 g of di-tert-butyl 2-anilinomalonate and 0.3 cm³ of thionyl chloride are used as starting materials. The product obtained is purified by chromatography on 50 g of silica (0.04–0.063 mm) contained in a column 3 cm in diameter [eluent: methanol/dichloromethane (1.5/98.5 by volume)], using an excess pressure of 40 kPa of nitrogen and collecting 25-cm³ fractions. Fractions 6 to 15 are combined and concentrated to dryness under reduced pressure (2.7 kPa) at 35° C. and the residue obtained is crystallization from 10 cm³ of diethyl ether. 0.67 g of di-tert-butyl 2-{2-[3-(3-methylphenyl)ureido]-N-phenylacetamido}malonate melting at 175° C. are then obtained.

Di-tert-butyl 2-anilinomalonate may be prepared in a manner analogous to that described in Example 8 for the preparation of tert-butyl (RS)-2-anilino-2-(4-methoxyphenyl)acetate, but using 2 g of di-tert-butyl 2-bromomalonate and 1.24 cm³ of aniline in 15 cm³ of acetonitrile as starting materials. The product obtained is purified by chromatography on 50 g of silica (0.04–0.063 mm) contained in a column 3 cm in diameter (eluent: dichloromethane), using an excess pressure of 40 kPa of nitrogen and collecting 25-cm³ fractions. Fractions 3 to 6 are combined and concentrated to dryness under reduced pressure (2.7 kPa) at 35° C. 1.3 g of di-tert-butyl 2-anilinomalonate melting at 94° C. are then obtained.

Di-tert-butyl 2-bromomalonate may be prepared in the following way: 0.76 cm³ of bromine is added dropwise to a solution of 2.24 cm³ of di-tert-butyl malonate and 1.18 g of acetamide in 45 cm³ of chloroform heated under reflux and the mixture is refluxed for a further 11 hours. After cooling, the insoluble matter is separated off by filtration and the filtrate is washed with twice 10 cm³ of a saturated aqueous sodium bicarbonate solution, dried over magnesium sulphate and then concentrated to dryness under reduced pressure (2.7 kPa) at 35° C. 2.1 g of di-tert-butyl 2-bromomalonate are then obtained in the form of an oil which is used as such in the subsequent syntheses.

The present invention also relates to the medicaments consisting of at least one compound of formula (I) in the pure form or in the form of a composition in which it is combined with any other pharmaceutically compatible product, which may be inert or physiologically active. The medicaments according to the invention may be employed orally, parenterally, rectally or topically.

Solid compositions for oral administration which may be used are tablets, pills, powders (gelatin capsules, sachets) or granules. In these compositions, the active principle according to the invention is mixed with one or more inert diluents, such as starch, cellulose, sucrose, lactose or silica, under a stream of argon. These compositions may also comprise substances other than the diluents, for example one or more lubricants such as magnesium stearate or talc, a colorant, a coating (coated tablets) or a glaze.

Liquid compositions for oral administration which may be used are pharmaceutically acceptable solutions, suspensions, emulsions, syrups and elixirs containing inert diluents such as water, ethanol, glycerol, vegetable oils or paraffin oil. These compositions may comprise substances other than the diluents, for example wetting agents, sweeteners, thickeners, flavorings or stabilisers.

The sterile compositions for parenteral administration may be preferably aqueous solutions or non-aqueous solutions, suspensions or emulsions. The following may be used as solvent or vehicle: water, propylene glycol, a polyethylene glycol, vegetable oils, in particular olive oil, injectable organic esters, for example ethyl oleate, or other suitable organic solvents. These compositions may also contain adjuvants, in particular wetting agents, agents for rendering isotonic, emulsifiers, dispersing agents and stabilizers. Sterilization may be effected in various ways, for example by aseptising filtration, by incorporating sterilizing agents into the composition, by irradiation or by heating. They may also be prepared in the form of sterile solid compositions which may be dissolved at the time of use in an injectable sterile medium.

The compositions for rectal administration are suppositories or rectal capsules which contain, in addition to the active compound, excipients such as cacao butter, semisynthetic glycerides or polyethylene glycols.

The compositions for topical administration may be, for example, creams, lotions, eye washes, mouth washes, nasal drops or aerosol sprays.

In human therapeutics, the compounds according to the invention are particularly useful for the treatment and the prevention of disorders associated with CCK and gastrin in the nervous system and the gastrointestinal system. These compounds may therefore be used in the treatment and the prevention of psychoses, anxiety disorders, Parkinson's disease, tardive dyskinesia, irritable colon syndrome, acute pancreatitis, ulcers and disorders of the intestinal motility and certain tumors of the lower oesophagus, the colon and the intestine, as a booster of the analgesic activity of narcotic and nonnarcotic analgesic medicaments and as an appetite regulator.

The doses depend on the desired effect, on the duration of the treatment and on the mode of administration used; they are generally between 0.05 g and 1 g per day administered orally for an adult, with single doses ranging from 10 mg to 500 mg of active substance.

In general, the physician will determine the appropriate posology depending on the age, the weight and all of the other factors inherent to the subject to be treated. The following examples illustrate compositions according to the invention:

Example A

Capsules containing 50 mg of active compound and having the following composition are prepared by the customary technique:

| tert-butyl (RS)-2-(2-chlorophenyl)-2-{2-[3-((3-methylphenyl)ureido]-N-phenylacetamido}acetate | 50 mg |
|---|---|
| cellulose | 18 mg |
| lactose | 55 mg |
| colloidal silica | 1 mg |
| sodium carboxymethyl starch | 10 mg |
| talc | 10 mg |
| magnesium stearate | 1 mg |

Example B

Tablets containing 50 mg of active compound and having the following composition are prepared by the customary technique:

| tert-butyl (RS)-2-(3-bromophenyl)-2-{2-[3-((3-methylphenyl)ureido]-N-phenylacetamido}acetate | 50 mg |
|---|---|
| lactose | 104 mg |
| cellulose | 40 mg |
| polyvidone | 10 mg |
| sodium carboxymethyl starch | 22 mg |
| talc | 10 mg |
| magnesium stearate | 2 mg |
| colloidal silica | 2 mg |
| a mixture of hydroxymethyl cellulose, glycerol and titanium oxide (72/3.5/24.5) qs 1 complete coated tablet weighing | 245 mg |

Example C

An injectable solution containing 10 mg of active compound and having the following composition is prepared:

| tert-butyl (RS)-2-(4-aminophenyl)-2-{2-[3-(3-methylphenyl)ureido]-N-phenylacetamido}-acetate | 50 mg |
|---|---|
| benzoic acid | 80 mg |
| benzyl alcohol | 0.06 cm³ |
| sodium benzoate | 80 mg |
| 95% ethanol | 0.4 cm³ |
| sodium hydroxide | 24 mg |
| propylene glycol | 1.6 cm³ |
| water qs | 4 cm³ |

Although the ivention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. Compounds of formula:

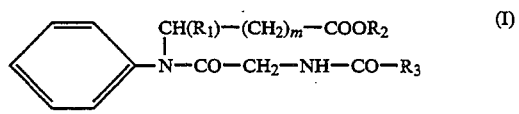

in which
  $R_1$ represents a hydrogen atom or an alkyl or alkoxycarbonyl group or a phenyl group which is unsubstituted or substituted by at least one substituent selected from halogen atoms, alkyl, alkoxy, nitro, amino and alkylthio groups,
  $R_2$ represents an alkyl containing 1-8 carbon atoms, polyfluoroalkyl, cinnamyl, or a cycloalkyl group which is unsubstituted or substituted by at least one alkyl group,
  $R_3$ represents a phenyl group unsubstituted or substituted by at least one substituent selected from alkyl, alkoxy, alkylthio and halogen; or a naphthyl group; or a phenylamino group, in which the phenyl ring of the phenylamino is optionally substituted by at least one substituent selected from halogen atoms, alkyl, alkoxy, and alkylthio groups, and
  m is 0 or 1,
it being understood that when $R_1$ represents a hydrogen atom or an alkyl or phenyl group, $R_3$ represents a naphthyl or phenylamino group, optionally substituted by an alkyl, alkoxy or alkylthio group or by one or two halogen atoms, and m is 0, $R_2$ is not an alkyl group containing 1 to 4 carbon atoms or a cycloalkyl group, as well as their racemates and their enantiomers when there is at least one center of asymmetry.

2. Compounds of formula (I) according to claim 1, wherein:
  $R_1$ represents a hydrogen atom or an alkoxycarbonyl group or a phenyl group optionally substituted by at least one substituent selected from halogen atoms, alkoxy, nitro and amino groups,
  $R_2$ represents an alkyl, polyfluoroalkyl or cinnamyl group or a cycloalkyl group which is unsubstituted or substituted by at least one alkyl group,
  $R_3$ represents a phenyl group substituted by an alkyl group or by a halogen atom, and
  m is 0 or 1,
as well as their racemates and their enantiomers when there is at least one center of asymmetry.

3. A pharmaceutical composition comprising as active principle, at least one compound of formula (I) according to claim 1, and a pharmaceutically acceptable carrier.

4. A pharmaceutical composition comprising as active principle, at least one compound of formula (I) according to claim 2 and a pharmaceutically acceptable carrier.

5. Method for the treatment of disorders associated with CCK and gastrin in the nervous system and the gastrointestinal system comprising administering an effective amount of at least one compound of formula (I) according to claim 1 to a patient suffering from said disorders.

6. Method for the treatment of disorders associated with CCK and gastrin in the nervous system and the gastrointestinal system comprising using the composition according to claim 4.

* * * * *